United States Patent
Komada et al.

[11] Patent Number: 6,043,186
[45] Date of Patent: *Mar. 28, 2000

[54] AMMOXIDATION CATALYST FOR USE IN PRODUCING ACRYLONITRILE OR METHACRYLONITRILE FROM PROPANE OR ISOBUTANE BY AMMOXIDATION

[75] Inventors: Satoru Komada, Yokohama; Kazuyuki Hamada, Kurashiki, both of Japan

[73] Assignee: Asahi Kasei Kogyo Kabushiki Kaisha, Osaka, Japan

[*] Notice: This patent is subject to a terminal disclaimer.

[21] Appl. No.: 09/172,648

[22] Filed: Oct. 15, 1998

[30] Foreign Application Priority Data

Oct. 15, 1997 [JP] Japan ................... 9-282304

[51] Int. Cl.⁷ ............... B01J 23/22; B01J 23/28
[52] U.S. Cl. ............... 502/312; 502/215; 502/305; 502/311; 502/321; 502/353; 558/323
[58] Field of Search ............... 502/215, 305, 502/311, 312, 353, 321; 558/323

[56] References Cited

U.S. PATENT DOCUMENTS

| | | | |
|---|---|---|---|
| 5,049,692 | 9/1991 | Hatano et al. | 558/318 |
| 5,231,214 | 7/1993 | Ushikubo et al. | 558/319 |
| 5,472,925 | 12/1995 | Ushikubo et al. | 502/312 |

FOREIGN PATENT DOCUMENTS

| | | |
|---|---|---|
| 0767164A1 | 4/1997 | European Pat. Off. . |
| 7144132A | 6/1995 | Japan . |
| 8057319A | 3/1996 | Japan . |
| 8141401A | 6/1996 | Japan . |

OTHER PUBLICATIONS

Gabriele Centi et al. *Applied Catalysis A: General 157* (1997) pp. 143–172.

*Primary Examiner*—John F. Niebling
*Assistant Examiner*—Alexander G. Ghyka

[57] ABSTRACT

An ammoxidation catalyst comprising a compound oxide which contains, in specific atomic ratios, molybdenum; vanadium; niobium; at least one element selected from tellurium and antimony; and at least one element selected from ytterbium, dysprosium, erbium, neodymium, samarium, lanthanum, praseodymium, europium, gadolinium, terbium, holmium, thulium, lutetium and scandium. By the use of the ammoxidation catalyst of the present invention, the ammonia-based yield of acrylonitrile or methacrylonitrile can be largely increased without sacrificing the propane- or isobutane-based yield of acrylonitrile or methacrylonitrile. Thus, the feed-stock ammonia can be efficiently utilized in the ammoxidation of propane or isobutane while achieving an efficient utilization of propane or isobutane.

8 Claims, 1 Drawing Sheet

AMMOXIDATION CATALYST FOR USE IN PRODUCING ACRYLONITRILE OR METHACRYLONITRILE FROM PROPANE OR ISOBUTANE BY AMMOXIDATION

BACKGROUND OF THE INVENTION

1. Field of the Invention

The present invention relates to an ammoxidation catalyst for use in producing acrylonitrile or methacrylonitrile from propane or isobutane by ammoxidation in the gaseous phase. More particularly, the present invention is concerned with an ammoxidation catalyst comprising a compound oxide which contains, in specific atomic ratios, molybdenum; vanadium; niobium; at least one element selected from tellurium and antimony; and at least one element selected from ytterbium, dysprosium, erbium, neodymium, samarium, lanthanum, praseodymium, europium, gadolinium, terbium, holmium, thulium, lutetium and scandium. By the use of the ammoxidation catalyst of the present invention, the ammonia-based yield of acrylonitrile or methacrylonitrile can be largely increased without sacrificing the propane- or isobutane-based yield of acrylonitrile or methacrylonitrile. In other words, in the present invention, the feedstock ammonia can be efficiently utilized in the ammoxidation of propane or isobutane while achieving an efficient utilization of propane or isobutane. The present invention is also concerned with a process for producing acrylonitrile or methacrylonitrile by using such an excellent ammoxidation catalyst.

2. Prior Art

There has been a well-known process for producing acrylonitrile or methacrylonitrile by ammoxidation of propylene or isobutylene. Recently, as a substitute for such a process using propylene or isobutylene, attention has been attracted to a process for producing acrylonitrile or methacrylonitrile by gaseous phase catalytic ammoxidation of propane or isobutane, i.e., by gaseous phase catalytic reaction of propane or isobutane with ammonia and molecular oxygen.

In the ammoxidation of propane or isobutane, stoichiometrically, the molar amount of the reacted ammonia is equal to the molar amount of the reacted propane or isobutane, namely, the molar ratio of the reacted ammonia to the reacted propane or isobutane is stoichiometrically unity (1). However, generally, during the course of the ammoxidation, ammonia, which is one of the gaseous feedstocks for the ammoxidation, is not only converted to by-products (such as acetonitrile and hydrocyanic acid) as well as acrylonitrile or methacrylonitrile as a desired product, but also is decomposed into nitrogen by oxidation [see *Applied Catalysis A General* (vol. 157, pp.143–172, 1997)].

That is, the conventional catalysts for use in the ammoxidation of propane or isobutane pose a problem in that, during the ammoxidation, conversion of ammonia to by-products and decomposition of ammonia into nitrogen occur to a large extent, leading to a lowering of the yield of acrylonitrile or methacrylonitrile, not only in terms of the yield based on propane or isobutane but also in terms of the yield based on ammonia (hereinafter, the yield of acrylonitrile or methacrylonitrile, based on the fed propane or isobutane, is frequently referred to as "propane- or isobutane-based yield of acrylonitrile or methacrylonitrile", and the yield of acrylonitrile or methacrylonitrile, based on the fed ammonia, is frequently referred to as "ammonia-based yield of acrylonitrile or methacrylonitrile").

The propane- or isobutane-based yield of acrylonitrile or methacrylonitrile can be increased by a method in which feedstock ammonia is fed in an amount larger than the molar amount of the fed propane or isobutane, that is, the molar ratio of the fed ammonia to the fed propane or isobutane is increased to more than 1. However, needless to say, in this method in which ammonia is simply fed in an excess amount, the ammonia-based yield of acrylonitrile or methacrylonitrile further decreases, that is, the utilization of feed-stock ammonia further decreases. In this connection, it should be noted that the cost of ammonia is usually almost equal to that of propane or isobutane. Therefore, when the amount of the fed ammonia is increased in the ammoxidation of propane or isobutane, the overall cost for producing acrylonitrile or methacrylonitrile by ammoxidation disadvantageously increases.

On the other hand, when the amount of the fed ammonia is decreased, the ammonia-based yield of acrylonitrile or methacrylonitrile can be increased. However, the conventional catalysts have a problem in that a decrease in the amount of the fed ammonia inevitably causes a large decrease in the propane- or isobutane-based yield of acrylonitrile or methacrylonitrile. That is, conventionally, the ammonia-based yield of acrylonitrile or methacrylonitrile cannot be increased without causing a large decrease in the propane- or isobutane-based yield thereof.

Thus, for efficiently and economically producing acrylonitrile or methacrylonitrile from propane or isobutane by ammoxidation, it is very advantageous that conversion of ammonia to by-products and decomposition of ammonia into nitrogen during the ammoxidation are suppressed to a level as low as possible, to thereby increase the ammonia-based yield of acrylonitrile or methacrylonitrile without sacrificing the propane- or isobutane-based yield thereof.

With respect to catalysts and methods for use in the ammoxidation of propane or isobutane, a number of proposals have been made.

For example, as a catalyst for use in producing acrylonitrile or methacrylonitrile from propane or isobutane by ammoxidation, an oxide catalyst containing molybdenum, vanadium, niobium and tellurium are known. Such oxide catalysts are disclosed in U.S. Pat. No. 5,049,692, U.S. Pat. No. 5,231,214, U.S. Pat. No. 5,472,925, Unexamined Japanese Patent Application Laid-Open Specification No. 7-144132, Unexamined Japanese Patent Application Laid-Open Specification No. 8-57319 and Unexamined Japanese Patent Application Laid-Open Specification No. 8-141401.

Further, European Patent Application Publication No. 767 164 A1 discloses an oxide catalyst containing molybdenum, vanadium, antimony and X wherein X is at least one element selected from the group consisting of niobium, tantalum, tungsten, titanium, zirconium, chromium, manganese, iron, ruthenium, cobalt, rhodium, nickel, palladium, platinum, boron, indium, cerium, alkali metals and alkaline earth metals.

Among the above prior art documents, each of U.S. Pat. No. 5,049,692, Unexamined Japanese Patent Application Laid-Open Specification No. 7-144132, Unexamined Japanese Patent Application Laid-Open Specification No. 8-57319 and Unexamined Japanese Patent Application Laid-Open Specification No. 8-141401 also discloses oxide catalysts containing, in addition to molybdenum, vanadium, niobium and tellurium, other types of elements. However, in any of these prior art documents, there is no working example in which an ammoxidation of propane or isobutane is performed using such oxide catalysts containing, in addition to molybdenum, vanadium, niobium and tellurium, other types of elements.

Further, U.S. Pat. No. 5,231,214 discloses an oxide catalyst containing molybdenum, vanadium, niobium, tellurium and at least one element selected from the group consisting of magnesium, calcium, strontium, barium, aluminum, gallium, thallium, indium, titanium, zirconium, hafnium, tantalum, chromium, manganese, tungsten, iron, ruthenium, cobalt, rhodium, nickel, palladium, platinum, zinc, tin, lead, arsenic, antimony, bismuth, lanthanum and cerium. However, among the above-mentioned elements other than molybdenum, vanadium, niobium and tellurium, the elements used in the catalysts prepared in the working examples of this prior art document are only manganese, nickel, magnesium, iron, tin, cobalt, aluminum, calcium, barium, antimony, bismuth, zinc, tantalum, tungsten, chromium, titanium and palladium.

The oxide catalysts disclosed in all the above prior art documents are disadvantageous not only in that a satisfactory level of propane- or isobutane-based yield of acrylonitrile or methacrylonitrile cannot be achieved, but also in that the ammonia-based yield of acrylonitrile or methacrylonitrile is not satisfactory.

On the other hand, U.S. Pat. No. 5,472,925 discloses two types of catalysts. Specifically, one type of catalyst is an oxide catalyst [hereinafter, frequently referred to as "catalyst (A)"] comprising a compound oxide containing molybdenum, vanadium, tellurium and X (wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium). The other type of catalyst is an oxide catalyst [hereinafter, frequently referred to as "catalyst (B)"] which is obtained by a method in which a compound containing at least one element selected from the group consisting of antimony, bismuth, cerium, boron, manganese, chromium, gallium, germanium, yttrium and lead is added to and mixed with the compound oxide of catalyst (A) above.

In this prior art document, there is a description of the ammoxidation of propane or isobutane using, as catalyst (A) mentioned above, an oxide catalyst containing molybdenum, vanadium, niobium and tellurium. By this prior art technique, when the molar ratio of the fed ammonia to the fed propane or isobutane (hereinafter, frequently referred to as "[ammonia:propane or isobutane] molar ratio") is 1 or less, the ammonia-based yield of acrylonitrile or methacrylonitrile is improved. However, this technique is disadvantageous not only in that the improvement in the ammonia-based yield of acrylonitrile or methacrylonitrile is unsatisfactory, but also in that the propane- or isobutane-based yield of acrylonitrile or methacrylonitrile markedly lowers when the [ammonia:propane or isobutane] molar ratio is 1 or less.

The above prior art document also has descriptions of the ammoxidations of propane or isobutane using, as catalyst (B) mentioned above, a catalyst comprising a mixture of diantimony tetraoxide ($Sb_2O_4$) and a compound oxide containing molybdenum, vanadium, tellurium and niobium. In some of these ammoxidations, even when the [ammonia:propane or isobutane] molar ratio is 1 or less, the propane- or isobutane-based yield of acrylonitrile or methacrylonitrile is improved. In some of these ammoxidations, when the [ammonia:propane or isobutane] molar ratio is 1 or less, although a lowering of the propane- or isobutane-based yield of acrylonitrile or methacrylonitrile occurs, the ammonia-based yield of acrylonitrile or methacrylonitrile is remarkably improved.

However, this prior art technique has a disadvantage in that, for obtaining the above-mentioned catalyst (B), it is necessary to employ a complicated and cumbersome production method. Specifically, the catalyst production method comprises: preparing a compound oxide containing molybdenum, vanadium, tellurium and niobium; molding the prepared compound oxide into a tablet; subjecting the obtained tablet to pulverization and sifting, to thereby obtain a particulate compound oxide; subjecting the obtained particulate compound oxide to calcination under a stream of nitrogen gas; grinding the resultant calcined, particulate compound oxide by means of a mortar to obtain a ground compound oxide; adding diantimony tetraoxide ($Sb_2O_4$) to the ground compound oxide, to thereby obtain a mixture; molding the obtained mixture into a tablet; subjecting the resultant tablet to pulverization and sifting, to thereby obtain a particulate catalyst precursor; and subjecting the obtained catalyst precursor to calcination under a stream of nitrogen gas, to thereby obtain a catalyst (B). Thus, this catalyst (B), which requires such burdensome production method, is disadvantageous from the commercial viewpoint.

Therefore, it has been strongly desired to develop an improved ammoxidation catalyst which is advantageous not only in that the ammonia-based yield of acrylonitrile or methacrylonitrile can be largely increased without sacrificing the propane- or isobutane-based yield of acrylonitrile or methacrylonitrile, but also in that the catalyst can be easily produced and hence is advantageous from the commercial viewpoint.

SUMMARY OF THE INVENTION

In this situation, the present inventors have conducted extensive and intensive studies with a view toward developing an improved catalyst for use in producing acrylonitrile or methacrylonitrile from propane or isobutane by ammoxidation in the gaseous phase, which can be easily produced and also provides a great advantage wherein the ammonia-based yield of acrylonitrile or methacrylonitrile can be increased without sacrificing the propane- or isobutane-based yield of acrylonitrile or methacrylonitrile, that is, an advantage of simultaneously achieving both an efficient utilization of the feedstock ammonia and an efficient utilization of the feedstock propane or isobutane. As a result, it has unexpectedly been found that the above objective can be attained by an ammoxidation catalyst comprising a compound oxide which contains, in specific atomic ratios, molybdenum; vanadium; niobium; at least one element selected from the group consisting of tellurium and antimony; and at least one element selected from the group consisting of ytterbium, dysprosium, erbium, neodymium, samarium, lanthanum, praseodymium, europium, gadolinium, terbium, holmium, thulium, lutetium and scandium. The present invention has been completed, based on the above novel finding.

Accordingly, it is an object of the present invention to provide an ammoxidation catalyst for use in producing acrylonitrile or methacrylonitrile from propane or isobutane by ammoxidation in the gaseous phase, which can be easily produced and also provides a great advantage wherein the ammonia-based yield of acrylonitrile or methacrylonitrile can be increased without sacrificing the propane- or isobutane-based yield of acrylonitrile or methacrylonitrile, that is, an advantage of simultaneously achieving both an efficient utilization of the feedstock ammonia and an efficient utilization of the feedstock propane or isobutane.

It is another object of the present invention to provide a process for producing acrylonitrile or methacrylonitrile from propane or isobutane by ammoxidation, using such an excellent catalyst.

DESCRIPTION OF REFERENCE NUMERALS

Figure 1:
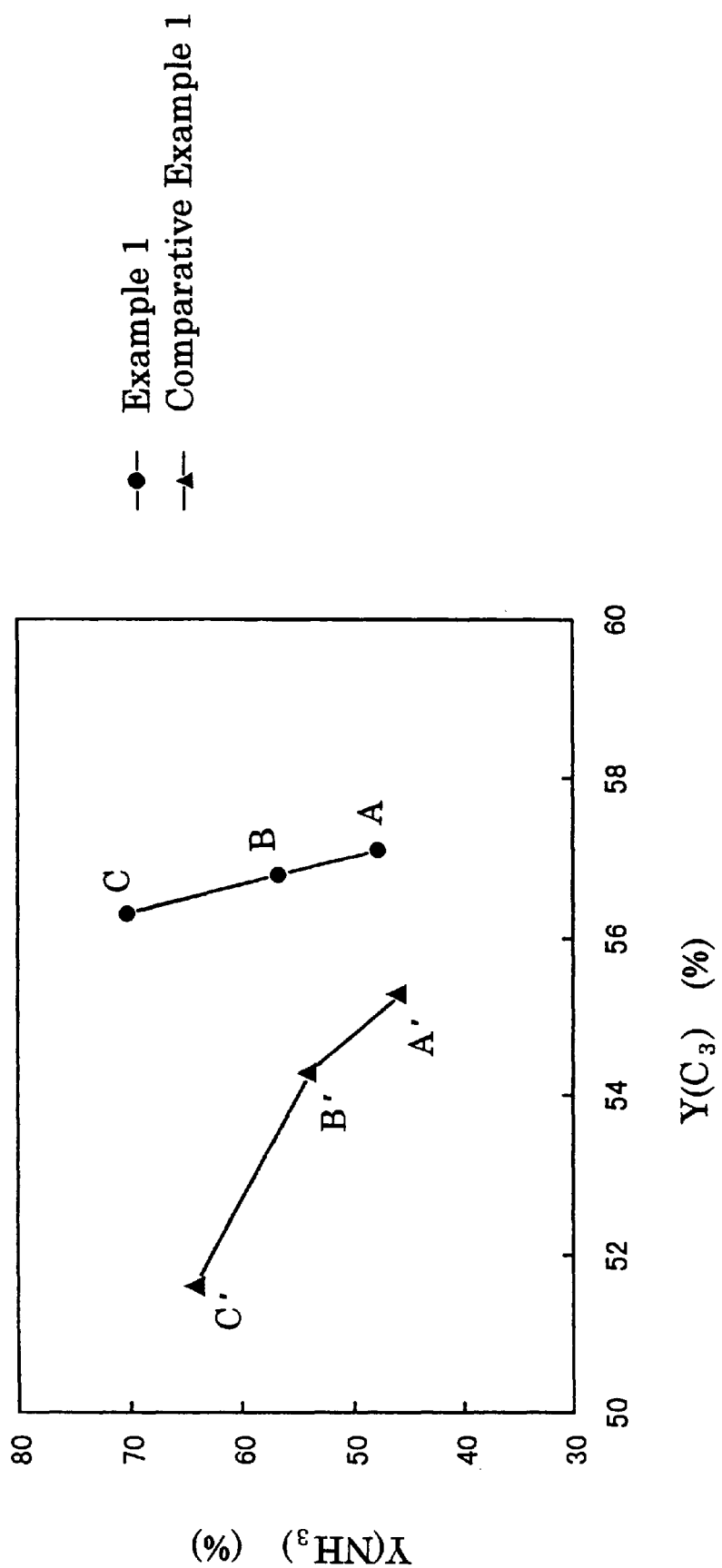
FIG. 1 is a graph showing the relationships between the propane-based yield [Y(C$_3$)] (%) of acrylonitrile and the ammonia-based yield [Y(NH$_3$)] (%) of acrylonitrile observed in ammoxidations performed in Example 1 and Comparative Example 1.

A, B, C: Points respectively obtained by plotting the Y(NH$_3$) values (ordinate) against the Y(C$_3$) values (abscissa), with respect to the ammoxidations performed in Example 1.

A', B', C': Points respectively obtained by plotting the Y(NH$_3$) values (ordinate) against the Y(C$_3$) values (abscissa), with respect to the ammoxidations performed in Comparative Example 1.

DETAILED DESCRIPTION OF THE INVENTION

In one aspect of the present invention, there is provided an ammoxidation catalyst for use in producing acrylonitrile or methacrylonitrile from propane or isobutane by ammoxidation in the gaseous phase, comprising a compound oxide represented by the following formula (1):

$$Mo_{1.0}V_aNb_bX_cZ_dE_eO_n \qquad (1)$$

wherein:
X is at least one element selected from the group consisting of tellurium and antimony;
Z is at least one element selected from the group consisting of ytterbium, dysprosium and erbium;
E is at least one element selected from the group consisting of neodymium, samarium, lanthanum, praseodymium, europium, gadolinium, terbium, holmium, thulium, lutetium and scandium; and
a, b, c, d, e and n are, respectively, the atomic ratios of vanadium, niobium, X, Z, E and oxygen, relative to molybdenum,
wherein:
$0.1 \leq a \leq 1.0$;
$0.01 \leq b \leq 1.0$;
$0.01 \leq c \leq 1.0$;
$0 \leq d \leq 0.1$;
$0 \leq e \leq 0.1$;
$0.001 \leq d+e \leq 0.1$; and
n is a number determined by and consistent with the valence requirements of the other elements present in the compound oxide of formula (1).

In another aspect of the present invention, there is provided a process for producing acrylonitrile or methacrylonitrile, which comprises reacting propane or isobutane with ammonia and molecular oxygen in the gaseous phase in the presence of the catalyst defined above.

For an easy understanding of the present invention, the essential features and various preferred embodiments of the present invention are enumerated below.

1. An ammoxidation catalyst for use in producing acrylonitrile or methacrylonitrile from propane or isobutane by ammoxidation in the gaseous phase, comprising a compound oxide represented by the following formula (1):

$$Mo_{1.0}V_aNb_bX_cZ_dE_eO_n \qquad (1)$$

wherein:
X is at least one element selected from the group consisting of tellurium and antimony;
Z is at least one element selected from the group consisting of ytterbium, dysprosium and erbium;
E is at least one element selected from the group consisting of neodymium, samarium, lanthanum, praseodymium, europium, gadolinium, terbium, holmium, thulium, lutetium and scandium; and
a, b, c, d, e and n are, respectively, the atomic ratios of vanadium, niobium, X, Z, E and oxygen, relative to molybdenum,
wherein:
$0.1 \leq a \leq 1.0$;
$0.01 \leq b \leq 1.0$;
$0.01 \leq c \leq 1.0$;
$0 \leq d \leq 0.1$;
$0 \leq e \leq 0.1$;
$0.001 \leq d+e \leq 0.1$; and
n is a number determined by and consistent with the valence requirements of the other elements present in the compound oxide formula (1).

2. The catalyst according to item 1 above, wherein X in formula (1) is tellurium.

3. The catalyst according to item 1 or 2 above, wherein d in formula (1) satisfies the following relationship: $0.001 \leq d \leq 0.1$.

4. The catalyst according to any one of items 1 to 3 above, wherein Z in formula (1) is ytterbium.

5. The catalyst according to any one of items 1 to 4 above, which further comprises a silica carrier having supported thereon the compound oxide, wherein the silica carrier is present in an amount of from 20 to 60% by weight in terms of SiO$_2$, based on the total weight of the compound oxide and the silica carrier.

6. A process for producing acrylonitrile or methacrylonitrile, which comprises reacting propane or isobutane with ammonia and molecular oxygen in the gaseous phase in the presence of an ammoxidation catalyst comprising a compound oxide represented by the following formula (1):

$$Mo_{1.0}V_aNb_bX_cZ_dE_eO_n \qquad (1)$$

wherein:
X is at least one element selected from the group consisting of tellurium and antimony;
Z is at least one element selected from the group consisting of ytterbium, dysprosium and erbium;
E is at least one element selected from the group consisting of neodymium, samarium, lanthanum, praseodymium, europium, gadolinium, terbium, holmium, thulium, lutetium and scandium; and
a, b, c, d, e and n are, respectively, the atomic ratios of vanadium, niobium, X, Z, E and oxygen, relative to molybdenum, wherein:
$0.1 \leq a \leq 1.0$;
$0.01 \leq b \leq 1.0$;
$0.01 \leq c \leq 1.0$;
$0 \leq d \leq 0.1$;
$0 \leq e \leq 0.1$;
$0.001 \leq d+e \leq 0.1$; and n is a number determined by and consistent with the valence requirements of the other elements present in the compound oxide of formula (1).

7. The process according to item 6 above, wherein X in formula (1) is tellurium.

8. The process according to item 6 or 7 above, wherein d in formula (1) satisfies the following relationship: $0.001 \leq d \leq 0.1$.

9. The process according to any one of items 6 to 8 above, wherein Z in formula (1) is ytterbium.

10. The process according to any one of items 6 to 9 above, wherein the catalyst further comprises a silica carrier having supported thereon the compound oxide, wherein the silica carrier is present in an amount of from 20 to 60% by weight in terms of $SiO_2$, based on the total weight of the compound oxide and the silica carrier.

Hereinbelow, the present invention will be described in more detail.

The ammoxidation catalyst of the present invention has a characteristic feature in that it comprises a compound oxide represented by the following formula (1):

$$Mo_{1.0}V_aNb_bX_cZ_dE_eO_n \qquad (1)$$

wherein:
X is at least one element selected from the group consisting of tellurium and antimony;
Z is at least one element selected from the group consisting of ytterbium, dysprosium and erbium;
E is at least one element selected from the group consisting of neodymium, samarium, lanthanum, praseodymium, europium, gadolinium, terbium, holmium, thulium, lutetium and scandium; and
a, b, c, d, e and n are, respectively, the atomic ratios of vanadium, niobium, X, Z, E and oxygen, relative to molybdenum,
wherein:
$0.1 \leq a \leq 1.0$, preferably $0.2 \leq a \leq 0.6$;
$0.01 \leq b \leq 1.0$, preferably $0.05 \leq b \leq 0.5$;
$0.01 \leq c \leq 1.0$, preferably $0.05 \leq c \leq 0.5$;
$0 \leq d \leq 0.1$, preferably $0.001 \leq d \leq 0.1$, more preferably $0.005 \leq d \leq 0.05$;
$0 \leq e \leq 0.1$, preferably $0.001 \leq e \leq 0.1$, more preferably $0.005 \leq e \leq 0.05$;
$0.001 \leq d+e \leq 0.1$, preferably $0.005 \leq d+e \leq 0.05$; and
n is a number determined by the valence requirements of the other elements present.

In the ammoxidation catalyst of the present invention, it is preferred that X in formula (1) is tellurium, and that Z in formula (1) is ytterbium.

The ammoxidation catalyst of the present invention may further comprise a silica carrier having supported thereon the compound oxide. When the catalyst of the present invention is in a silica-supported form, the catalyst exhibits high mechanical strength, so that it can be advantageously used for ammoxidation in a fluidized-bed reactor. The silica carrier is preferably present in an amount of from 20 to 60% by weight in terms of $SiO_2$, more preferably from 20 to 40% by weight in terms of $SiO_2$, based on the total weight of the compound oxide and the silica carrier.

The catalyst of the present invention may further optionally contain (Q) at least one element which is other than the above-mentioned component elements contained in the catalyst of the preset invention. For example, the catalyst of the preset invention may further contain, as optional component element Q, at least one element selected from the group consisting of tungsten, chromium, tantalum, titanium, zirconium, hafnium, manganese, rhenium, iron, ruthenium, cobalt, rhodium, nickel, palladium, platinum, silver, zinc, boron, aluminum, gallium, indium, germanium, tin, lead, phosphorus, bismuth and alkaline earth metals. When the catalyst of the present invention contains optional component element Q, it is preferred that the amount of component element Q is 0.1 or less in terms of the atomic ratio of component element Q to molybdenum.

With respect to the source of each component element for the ammoxidation catalyst of the present invention, there is no particular limitation. Representative examples of sources of component elements for the ammoxidation catalyst of the present invention include ammonium heptamolybdate $[(NH_4)_6Mo_7O_{24}\cdot 4H_2O]$ as a source of molybdenum; ammonium metavanadate $(NH_4VO_3)$ as a source of vanadium; a niobic acid, an inorganic acid salt of niobium or an organic acid salt of niobium as a source of niobium; telluric acid $(H_6TeO_6)$ as a source of tellurium (component element X); and diantimony trioxide $(Sb_2O_3)$ as a source of antimony (component element X).

With respect to the source of niobium, it is preferred to use niobic acid. The "niobic acid" is a hydrated compound represented by the following formula: $Nb_2O_5\cdot nH_2O$, which is also known as "niobium hydroxide" or "niobium oxide hydrate". It is especially preferred to use a niobium-containing aqueous solution disclosed in European Patent Application No. 98 114 580.8, which comprises water having dissolved therein a dicarboxylic acid, a niobium compound and optionally ammonia, wherein the dicarboxylic acid/niobium molar ratio is 1 to 4, and the ammonia/niobium molar ratio is 0 to 2.

Examples of sources of component element Z (i.e., ytterbium, dysprosium and/or erbium) and component element E (i.e., neodymium, samarium, lanthanum, praseodymium, europium, gadolinium, terbium, holmium, thulium, lutetium and/or scandium) include organic acid salts, nitrates and halides of the elements. Of these, acetates and nitrates of the elements are preferred.

Examples of sources of optional component elements Q include nitrates, oxalates, acetates, hydroxides, oxides, ammonium salts and carbonates of the elements.

The ammoxidation catalyst of the present invention can be produced by a conventional method. For example, the catalyst can be produced by a method comprising the steps of (1) preparing a raw material mixture (for example, a slurry of raw materials), (2) drying the raw material mixture obtained in step (1) above to obtain a dried catalyst precursor, and (3) subjecting the dried catalyst precursor obtained in step (2) above to calcination.

Hereinbelow, explanation is made with respect to a preferred embodiment of the above-mentioned method for producing the ammoxidation catalyst of the present invention, which comprises steps (1), (2) and (3), above.

In step (1), a raw material mixture is prepared.

First, an aqueous mixture is prepared by dissolving ammonium-heptamolybdate, ammonium metavanadate and telluric acid in water (this aqueous mixture is designated "mixture A").

Alternatively, when antimony is used as a component element, an aqueous mixture is first prepared by a method in which a diantimony trioxide powder is dispersed in an aqueous solution of ammonium metavanadate to thereby obtain a dispersion, and the obtained dispersion is heated under reflux conditions to obtain a solution or slurry, and then, ammonium heptamolybdate and optionally telluric acid are added to the obtained solution or slurry to obtain an aqueous mixture (this aqueous mixture is designated "mixture A'").

On the other hand, oxalic acid and niobic acid are dissolved in water while heating and stirring, to thereby obtain an aqueous mixture (this aqueous mixture is designated "mixture B").

A source of component element Z and/or component element E for the compound oxide, such as ytterbium acetate, is dissolved in water to obtain an aqueous mixture (this aqueous mixture is designated "mixture C").

Further, when the ammoxidation catalyst of the present invention contains the above-mentioned optional component element Q, a nitrate, an oxalate, an acetate, a hydroxide, an oxide, an ammonium salt, a carbonate or the like of optional component element Q is dissolved in water, to obtain an aqueous mixture (this aqueous mixture is designated "mixture D").

To mixture A or A' are successively added mixture B, mixture C and optionally mixture D, to thereby obtain a raw material mixture.

When the ammoxidation catalyst of the present invention further comprises a silica carrier having supported thereon the compound oxide, the raw material mixture is prepared so as to contain a silica sol also. The addition of a silica sol can be made at any time during the above preparation operation for the raw material mixture, which comprises preparing mixture A or A' and mixtures B and C and optionally mixture D and mixing together these mixture A or A' and mixtures B and C and optionally mixture D.

Thus obtained raw material mixture may be in the form of either a solution or a slurry. However, the raw material mixture is generally obtained in the form of a slurry.

In step (2), the raw material mixture obtained in step (1) above is subjected to spray drying. The spray drying of the raw material mixture can be generally conducted by centrifugation, two-phase flow nozzle method or high pressure nozzle method to obtain a dried particulate catalyst precursor. In this instance, it is preferred to use air which has been heated by steam, an electric heater or the like, as a heat source for drying. It is preferred that the temperature of the spray dryer at an entrance to the dryer section thereof is from 150 to 300° C.

In step (3), the dried particulate catalyst precursor obtained in step (2) above is calcined to thereby obtain a catalyst. The dried particulate catalyst is calcined in an atmosphere of an inert gas, such as nitrogen gas, argon gas or helium gas, which is substantially free of oxygen, preferably under a flow of an inert gas, at a temperature of 500 to 700° C., preferably 550 to 650° C., for 0.5 to 20 hours, preferably 1 to 8 hours.

For the calcination, use can be made of a kiln, such as a rotary kiln, a tunnel kiln, a muffle kiln and a fluidized firing kiln. The calcination of the catalyst can be repeatedly conducted.

Prior to the calcination in step (3), the dried catalyst precursor may be subjected to pre-calcination. That is, prior to the calcination in step (3), the dried catalyst precursor obtained in step (2) above may be pre-calcined in an atmosphere of air or under a flow of air at 200 to 400° C. for 1 to 5 hours.

Acrylonitrile or methacrylonitrile can be produced by reacting propane or isobutane with ammonia and molecular oxygen in the gaseous phase in the presence of the catalyst of the present invention.

Accordingly, as mentioned above, in another aspect of the present invention, there is provided a process for producing acrylonitrile or methacrylonitrile, which comprises reacting propane or isobutane with ammonia and molecular oxygen in the gaseous phase in the presence of the catalyst defined above.

Propane or isobutane and ammonia used in the process of the present invention need not be of a very high purity but may be of a commercial grade.

Examples of sources of molecular oxygen include air, oxygen-rich air, and pure oxygen. Further, such a source of molecular oxygen may be diluted with helium, argon, nitrogen, carbon dioxide, steam or the like.

In the process of the present invention, the molar ratio of ammonia to propane or isobutane used for the ammoxidation may be generally in the range of from 0.3 to 1.5, preferably from 0.8 to 1.0. By the use of the catalyst of the present invention, the ammoxidation of propane or isobutane can be conducted under conditions wherein the molar ratio of ammonia to propane or isobutane is at a low level, as compared to the level required in the case of a process using the conventional ammoxidation catalyst.

The molar ratio of molecular oxygen to propane or isobutane used for the ammoxidation may be generally in the range of from 0.1 to 6, preferably from 0.5 to 4.

In the process of the present invention, the ammoxidation temperature is generally in the range of from 350 to 500° C., preferably from 380 to 470° C.

In the process of the present invention, the ammoxidation pressure is generally in the range of from 0.5 to 5 atm., preferably from atmospheric pressure to 3 atm.

The time of contact (contact time) between the gaseous feedstocks and the catalyst is generally in the range of from 0.1 to 10 sec.g/cc, preferably from 0.5 to 5 sec.g/cc. In the process of the present invention, the contact time during the ammoxidation of propane or isobutane is determined according to the following formula:

Contact time (sec.g/cc)=(W/F)×273/(273+T)

$$(W/F) \times \frac{273}{(273+T)}$$

wherein:
W represents the weight (g) of the catalyst contained in the reactor;
F represents the flow rate (Ncc/sec) of the gaseous feedstocks [Ncc means cc as measured under the normal temperature and pressure conditions (0° C., 1 atm)]; and
T represents the ammoxidation temperature (° C.).

The process of the present invention for producing acrylonitrile or methacrylonitrile by ammoxidation of propane or isobutane in the gaseous phase can be conducted in a conventional reactor, such as a fixed-bed reactor, a fluidized-bed reactor or a moving-bed reactor. For facilitating the removal of reaction heat generated during the ammoxidation, preferred is a fluidized-bed reactor.

The reaction mode employed in the process of the present invention may be either a one-pass mode or a recycling mode.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, the ratio of the fed ammonia to the fed propane (hereinafter, frequently referred to as "ammonia/propane molar ratio") (R) is defined as follows:

$$R = \frac{\text{(mole of ammonia fed)}}{\text{(mole of propane fed)}}$$

In addition, the propane-based yield [Y(C$_3$)] (%) of acrylonitrile and the ammonia-based yield [Y(NH$_3$)] (%) of acrylonitrile, each used for evaluating the results of the ammoxidation of propane, are defined as follows:

Propane-based yield [Y(C$_3$)] (%) of acrylonitrile=

$$\frac{\text{(mole of acrylonitrile formed)}}{\text{(mole of propane fed)}} \times 100$$

Ammonia-based yield [Y(NH$_3$)] (%) of acrylonitrile=

$$\frac{\text{(mole of acrylonitrile formed)}}{\text{(mole of ammonia fed)}} \times 100$$

EXAMPLE 1

(Preparation of an Ammoxidation Catalyst)

An ammoxidation catalyst comprising a compound oxide represented by the formula:

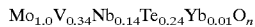

$Mo_{1.0}V_{0.34}Nb_{0.14}Te_{0.24}Yb_{0.01}O_n$ was prepared as follows.

374.12 g of ammonium heptamolybdate [(NH$_4$)$_6$Mo$_7$O$_{24}$·4H$_2$O], 84.56 g of ammonium metavanadate (NH$_4$VO$_3$) and 117.11 g of telluric acid (H$_6$TeO$_6$) were dissolved in 1,700 g of water at about 60° C. while stirring, followed by cooling to about 30° C., to thereby obtain mixture A-1 (corresponding to mixture A described above).

51.11 g of a niobic acid (Nb$_2$O$_5$·nH$_2$O) (Nb$_2$O$_5$ content: 76.6% by weight) and by 100.29 g of oxalic acid (H$_2$C$_2$O$_4$·2H$_2$O) were dissolved in 500 g of water at about 60° C. while stirring, followed by cooling to about 30° C., to thereby obtain mixture B-1 (corresponding to mixture B described above).

8.89 g of ytterbium acetate [Yb(CH$_3$COO)$_3$·4H$_2$O] was dissolved in 280 g of water at about 60° C. while stirring, followed by cooling to about 30° C., to thereby obtain mixture C-1 (corresponding to mixture C described above).

To mixture A-1 obtained above were successively added mixture B-1 and mixture C-1 while stirring, to thereby obtain a raw material mixture.

The obtained raw material mixture was subjected to spray drying using a centrifugation type spray-drying apparatus under conditions wherein the inlet temperature of the apparatus was 240° C. and the outlet temperature of the apparatus was 145° C., to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS according to Japanese industrial standards) tube having an inner diameter of 1 inch, and then calcined at 600° C. for 2 hours under a stream of nitrogen gas at a flow rate of 150 Ncc/min, to thereby obtain a catalyst.

(Ammoxidation of Propane)

Using the catalyst obtained above, ammoxidations of propane were serially performed as follows.

1.0 g of the obtained catalyst was charged into a fixed-bed reaction tube having an inner diameter of 10 mm. In the reaction tube containing the catalyst, an ammoxidation of propane was performed under conditions wherein the contact time between the catalyst and a gaseous feedstock mixture (i.e., a gaseous mixture of propane, ammonia, molecular oxygen and helium) was 1.0 sec.g/cc, the [propane:ammonia:molecular oxygen:helium] molar ratio in the gaseous feedstock mixture was 1.0:1.2:2.8:12.0 (the ammonia/propane molar ratio R=1.2), the ammoxidation temperature was 440° C. and the ammoxidation pressure was atmospheric pressure. A part of the resultant gaseous reaction product effluent from the reaction tube (wherein the reaction product was obtained from the gaseous feedstock mixture having an ammonia/propane molar ratio R of 1.2) was analyzed to measure the propane-based yield [Y(C$_3$)] (%) of acrylonitrile and the ammonia-based yield [Y(NH$_3$)] (%) of acrylonitrile.

Subsequently, the composition of the gaseous feedstock mixture was changed so as to have a [propane:ammonia:molecular oxygen:helium] molar ratio of 1.0:1.0:2.8:12.0 (the ammonia/propane molar ratio R=1.0). Then, an ammoxidation of propane was conducted under the same conditions as mentioned above except that the ammonia/propane molar ratio (R) was 1.0. A part of the resultant gaseous reaction product effluent from the reaction tube (wherein the reaction product was obtained from the gaseous feedstock mixture having an ammonia/propane molar ratio R of 1.0) was analyzed to measure the propane-based yield [Y(C$_3$)](%) of acrylonitrile and the ammonia-based yield [Y(NH$_3$)](%) of acrylonitrile.

Subsequently, the composition of the gaseous feedstock mixture was changed so as to have a [propane:ammonia:molecular oxygen:helium] molar ratio of 1.0:0.8:2.8:12.0 (the ammonia/propane molar ratio R=0.8). Then, an ammoxidation of propane was conducted under the same conditions as mentioned above except that the ammonia/propane molar ratio (R) was 0.8. A part of the resultant gaseous reaction product effluent from the reaction tube (wherein the reaction product was obtained from the gaseous feedstock mixture having an ammonia/propane molar ratio R of 0.8) was analyzed to measure the propane-based yield [Y(C$_3$)] (%) of acrylonitrile and the ammonia-based yield [Y(NH$_3$)] (%) of acrylonitrile.

The results of the above ammoxidations are shown in Table 1.

COMPARATIVE EXAMPLE 1

(Preparation of an Ammoxidation Catalyst)

An ammoxidation catalyst comprising a compound oxide represented by the formula:

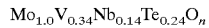

$Mo_{1.0}V_{0.34}Nb_{0.14}Te_{0.24}O_n$ was prepared in substantially the same manner as in Example 1 except that ytterbium acetate [Yb(CH$_3$COO)$_3$·4H$_2$O] was not used.

(Ammoxidation of Propane)

Using the catalyst obtained above, ammoxidations of propane were serially conducted under substantially the same conditions as in Example 1. The results of the ammoxidations are shown in Table 1.

The relationship between Y(C$_3$) and Y(NH$_3$) in each of Example 1 and Comparative Example 1 is shown in FIG. 1, wherein the Y(NH$_3$) values (ordinate) are plotted against the Y(C$_3$) values (abscissa).

EXAMPLE 2

(Preparation of an Ammoxidation Catalyst)

An ammoxidation catalyst comprising a compound oxide represented by the formula:

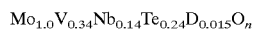

$Mo_{1.0}V_{0.34}Nb_{0.14}Te_{0.24}D_{0.015}O_n$ was prepared in substantially the same manner as in Example 1 except that 13.01 g of dysprosium acetate [Dy(CH$_3$COO)$_3$.4H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 1 except that the compositions of the gaseous feedstock mixtures were changed so as to have ammonia/propane molar ratios (R) of 1.0 and 0.8. The results of the ammoxidations are shown in Table 2.

EXAMPLE 3

(Preparation of an Ammoxidation Catalyst)

An ammoxidation catalyst comprising a compound oxide represented by the formula:

$$Mo_{1.0}V_{0.34}Nb_{0.14}Te_{0.24}Er_{0.015}O_n$$

was prepared in substantially the same manner as in Example 1 except that 13.16 g of erbium acetate [Er(CH$_3$COO)$_3$.4H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown in Table 2.

EXAMPLE 4

(Preparation of an Ammoxidation Catalyst)

An ammoxidation catalyst comprising a compound oxide represented by the formula:

$$M_{1.0}V_{0.34}Nb_{0.14}Te_{0.24}Nd_{0.013}O_n$$

was prepared in substantially the same manner as in Example 1 except that 9.29 g of neodymium acetate [Nd(CH$_3$COO)$_3$.H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown in Table 2.

EXAMPLE 5

(Preparation of an Ammoxidation Catalyst)

An ammoxidation catalyst comprising a compound oxide represented by the formula:

$$Mo_{1.0}V_{0.34}Nb_{0.14}Te_{0.24}Sm_{0.013}O_n$$

was prepared in substantially the same manner as in Example 1 except that 10.94 g of samarium acetate [Sm(CH$_3$COO)$_3$.4H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown in Table 2.

EXAMPLE 6

(Preparation of an Ammoxidation Catalyst)

An ammoxidation catalyst comprising a compound oxide represented by the formula:

$$Mo_{1.0}V_{0.34}Nb_{0.14}Te_{0.24}La_{0.01}O_n$$

was prepared in substantially the same manner as in Example 1 except that 7.40 g of a lanthanum acetate [La(CH$_3$COO)$_3$.nH$_2$O] (La$_2$O$_3$ content: 46.3% by weight) was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown in Table 2.

EXAMPLE 7

(Preparation of an Ammoxidation Catalyst)

An ammoxidation catalyst comprising a compound oxide represented by the formula:

$$Mo_{1.0}V_{0.34}Nb_{0.14}Te_{0.24}Pr_{0.011}O_n$$

was prepared in substantially the same manner as in Example 1 except that 8.20 g of praseodymium acetate [Pr(CH$_3$COO)$_3$.2H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown-in Table 2.

EXAMPLE 8

(Preparation of an Ammoxidation Catalyst)

An ammoxidation catalyst comprising a compound oxide represented by the formula:

$$Mo_{1.0}V_{0.34}Nb_{0.14}Te_{0.24}Eu_{0.012}O_n$$

was prepared in substantially the same manner as in Example 1 except that 9.68 g of europium acetate [Eu(CH$_3$COO)$_3$.3H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown in Table 2.

EXAMPLE 9

(Preparation of an Ammoxidation Catalyst)

An ammoxidation catalyst comprising a compound oxide represented by the formula:

$$Mo_{1.0}V_{0.34}Nb_{0.14}Te_{0.24}Gd_{0.015}O_n$$

was prepared in substantially the same manner as in Example 1 except that 12.84 g of gadolinium acetate [Gd(CH$_3$COO)$_3$.4H$_2$O] was used instead of the ytterbium acetate [Yb(CH$_3$COO)$_3$.4H$_2$O].

(Ammoxidation of Propane)

Using the catalyst obtained above, ammoxidations of propane were serially conducted under substantially the same conditions as in Example 2. The results of the ammoxidations are shown in Table 2.

EXAMPLE 10

(Preparation of an Ammoxidation Catalyst)

An ammoxidation catalyst comprising a compound oxide represented by the formula:

$$Mo_{1.0}V_{0.34}Nb_{0.14}Te_{0.24}Tb_{0.012}O_n$$

was prepared in substantially the same manner as in Example 1 except that 10.32 g of terbium acetate [Tb

15

$(CH_3COO)_3 \cdot 4H_2O$] was used instead of the ytterbium acetate [Yb$(CH_3COO)_3 \cdot 4H_2O$].
(Ammoxidation of Propane)

Using the catalyst obtained above, ammoxidations of propane were serially conducted under substantially the same conditions as in Example 2. The results of the ammoxidations are shown in Table 2.

EXAMPLE 11
(Preparation of an Ammoxidation Catalyst)

An ammoxidation catalyst comprising a compound oxide represented by the formula:

$$Mo_{1.0}V_{0.34}Nb_{0.14}Te_{0.24}Ho_{0.011}O_n$$

was prepared in substantially the same manner as in Example 1 except that 9.59 g of holmium acetate [Ho$(CH_3COO)_3 \cdot 4H_2O$] was used instead of the ytterbium acetate [Yb$(CH_3COO)_3 \cdot 4H_2O$].
(Ammoxidation of Propane)

Using the catalyst obtained above, ammoxidations of propane were serially conducted under substantially the same conditions as in Example 2. The results of the ammoxidations are shown in Table 2.

Example 12
(Preparation of an Ammoxidation Catalyst)

An ammoxidation catalyst comprising a compound oxide represented by the formula:

$$Mo_{1.0}V_{0.34}Nb_{0.14}Te_{0.24}Tm_{0.012}O_n$$

was prepared in substantially the same manner as in Example 1 except that 10.57 g of thulium acetate [Tm$(CH_3COO)_3 \cdot 4H_2O$] was used instead of the ytterbium acetate [Yb$(CH_3COO)_3 \cdot 4H_2O$].
(Ammoxidation of Propane)

Using the catalyst obtained above, ammoxidations of propane were serially conducted under substantially the same conditions as in Example 2. The results of the ammoxidations are shown in Table 2.

EXAMPLE 13
(Preparation of an Ammoxidation Catalyst)

An ammoxidation catalyst comprising a compound oxide represented by the formula:

$$Mo_{1.0}V_{0.34}Nb_{0.14}Te_{0.24}Lu_{0.013}O_n$$

was prepared in substantially the same manner as in Example 1 except that 11.12 g of lutetium acetate [Lu$(CH_3COO)_3 \cdot 3H_2O$] was used instead of the ytterbium acetate [Yb$(CH_3COO)_3 \cdot 4H_2O$].
(Ammoxidation of Propane)

Using the catalyst obtained above, ammoxidations of propane were serially conducted under substantially the same conditions as in Example 2. The results of the ammoxidations are shown in Table 2.

EXAMPLE 14
(Preparation of an Ammoxidation Catalyst)

An ammoxidation catalyst comprising a compound oxide represented by the formula:

$$Mo_{1.0}V_{0.34}Nb_{0.14}Te_{0.24}Sc_{0.005}O_n$$

was prepared in substantially the same manner as in Example 1 except that 3.19 g of scandium nitrate [Sc$(NO_3)_3 \cdot 4H_2O$] was used instead of the ytterbium acetate [Yb$(CH_3COO)_3 \cdot 4H_2O$].

16

(Ammoxidation of Propane)

Using the catalyst obtained above, ammoxidations of propane were serially conducted under substantially the same conditions as in Example 2. The results of the ammoxidations are shown in Table 2.

COMPARATIVE EXAMPLE 2
(Preparation of an Ammoxidation Catalyst)

An ammoxidation catalyst comprising a compound oxide represented by the formula:

$$Mo_{1.0}V_{0.34}Nb_{0.14}Te_{0.24}Yb_{0.20}O_n$$

was prepared in substantially the same manner as in Example 1 except that use was made of an aqueous mixture obtained by dissolving 177.86 g of ytterbium acetate in 3,600 g of water instead of mixture C-1 obtained by dissolving 8.89 g of ytterbium acetate [Yb$(CH_3COO)_3 \cdot 4H_2O$] in 280 g of water.
(Ammoxidation of Propane)

Using the catalyst obtained above, ammoxidations of propane were serially conducted under substantially the same conditions as in Example 2. The results of the ammoxidations are shown in Table 2.

EXAMPLE 15
(Preparation of an Ammoxidation Catalyst)

An ammoxidation catalyst comprising a silica carrier having supported thereon a compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.34}Nb_{0.14}Te_{0.24}Yb_{0.015}O_n$$

was prepared as follows.

521.60 g of ammonium heptamolybdate [$(NH_4)_6Mo_7O_{24} \cdot 4H_2O$], 117.90 g of ammonium metavanadate ($NH_4VO_3$) and 163.28 g of telluric acid ($H_6TeO_6$) were dissolved in 2,400 g of water at about 60° C. while stirring, followed by cooling to about 30° C., to thereby obtain mixture A-2 (corresponding to mixture A described above).

71.26 g of a niobic acid ($Nb_2O_5 \cdot nH_2O$) ($Nb_2O_5$ content: 76.6% by weight) and 165.73 g of oxalic acid ($H_2C_2O_4 \cdot 2H_2O$) were dissolved in 680 g of water at about 60° C. while stirring, followed by cooling to about 30° C., to thereby obtain mixture B-2 (corresponding to mixture B described above).

18.99 g of ytterbium nitrate [Yb$(NO_3)_3 \cdot 4H_2O$] was dissolved in 50 g of water at about 60° C. while stirring, followed by cooling to about 30° C., to thereby obtain mixture C-2 (corresponding to mixture C described above).

To mixture A-2 obtained above were successively added mixtures B-2 and C-2 and 1,000 g of a silica sol having a $SiO_2$ content of 30% by weight while stirring, to thereby obtain a raw material mixture.

The obtained raw material mixture was subjected to spray drying, pre-calcination and calcination, which were conducted in the same manner as in Example 1, to thereby obtain a catalyst.
(Ammoxidation of Propane)

Using the catalyst obtained above, ammoxidations of propane were serially performed as follows.

45.0 g of the obtained catalyst was charged into a Vycor glass fluidized-bed reaction tube having an inner diameter of 25 mm. In the reaction tube containing the catalyst, an ammoxidation of propane was performed under conditions wherein the contact time between the catalyst and a gaseous feedstock mixture (i.e., a gaseous mixture of propane, ammonia, molecular oxygen and helium) was 3.0 sec.g/cc, the [propane:ammonia: molecular oxygen:helium] molar ratio in the gaseous feedstock mixture was 1.0:1.0:2.8:12.0 (i.e., ammonia/propane molar ratio R=1.0), the ammoxidation temperature was 440° C. and the ammoxidation pressure was atmospheric pressure. A part of the resultant gaseous reaction product effluent from the reaction tube (wherein the reaction product was obtained from the gaseous feedstock mixture having an ammonia/propane molar ratio R of 1.0) was analyzed to measure the propane-based yield [Y(C$_3$)](%) of acrylonitrile and the ammonia-based yield [Y(NH$_3$)](%) of acrylonitrile.

Subsequently, the composition of the gaseous feedstock mixture was changed so as to have a [propane:ammonia:molecular oxygen:helium] molar ratio of 1.0:0.8:2.8:12.0 (the ammonia/propane molar ratio R=0.8). Then, an ammoxidation of propane was conducted under the same conditions as mentioned above except that ammonia/propane molar ratio R was 0.8. A part of the resultant gaseous reaction product effluent from the reaction tube (wherein the reaction product was obtained from the gaseous feedstock mixture having an ammonia/propane molar ratio R of 0.8) was analyzed to measure the propane-based yield [Y(C$_3$)](%) of acrylonitrile and the ammonia-based yield [Y(NH$_3$)](%) of acrylonitrile were measured.

The results of the above ammoxidations are shown in Table 3.

COMPARATIVE EXAMPLE 3
(Preparation of an Ammoxidation Catalyst)

An ammoxidation catalyst comprising a silica carrier having supported thereon a compound oxide, wherein the silica carrier is present in an amount of 30% by weight in terms of SiO$_2$, based on the total weight of the compound oxide and the silica carrier, and wherein the compound oxide is represented by the formula:

$$Mo_{1.0}V_{0.34}Nb_{0.14}Te_{0.24}O_n$$

was prepared in substantially the same manner as in Example 15 except that ytterbium nitrate [Yb(NO$_3$)$_3$.4H$_2$O] was not used.
(Ammoxidation of Propane)

Using the catalyst obtained above, ammoxidations of propane were serially conducted under substantially the same conditions as in Example 15. The results of the ammoxidations are shown in Table 3.

EXAMPLE 16
(Preparation of an Ammoxidation Catalyst)

An ammoxidation catalyst comprising a silica carrier having supported thereon a compound oxide, wherein the silica carrier is present in an amount of 30% by weight in terms of SiO$_2$, based on the total weight of the compound oxide and the silica carrier, and wherein the compound oxide is represented by the formula:

$$Mo_{1.0}V_{0.34}Nb_{0.14}Te_{0.24}Yb_{0.02}O_n$$

was prepared in substantially the same manner as in Example 15 except that 25.32 g of ytterbium nitrate [Yb(NO$_3$)$_3$.4H$_2$O] was used (instead of 18.99 g).
(Ammoxidation of Propane)

Using the catalyst obtained above, ammoxidations of propane were serially conducted under substantially the same conditions as in Example 15. The results of the ammoxidations are shown in Table 3.

EXAMPLE 17
(Preparation of an Ammoxidation Catalyst)

An ammoxidation catalyst comprising a silica carrier having supported thereon a compound oxide, wherein the silica carrier is present in an amount of 30% by weight in terms of SiO$_2$, based on the total weight of the compound oxide and the silica carrier, and wherein the compound oxide is represented by the formula:

$$Mo_{1.0}V_{0.34}Nb_{0.14}Te_{0.24}Dy_{0.150}O_n$$

was prepared in substantially the same manner as in Example 15 except that 19.32 g of dysprosium nitrate [Dy(NO$_3$)$_3$.5H$_2$O] was used instead of the ytterbium nitrate [Yb(NO$_3$)$_3$.4H$_2$O].
(Ammoxidation of Propane)

Using the catalyst obtained above, ammoxidations of propane were serially conducted under substantially the same conditions as in Example 15. The results of the ammoxidations are shown in Table 3.

EXAMPLE 18
(Preparation of an Ammoxidation Catalyst)

An ammoxidation catalyst comprising a silica carrier having supported thereon a compound oxide, wherein the silica carrier is present in an amount of 30% by weight in terms of SiO$_2$, based on the total weight of the compound oxide and the silica carrier, and wherein the compound oxide is represented by the formula:

$$Mo_{1.0}V_{0.34}Nb_{0.14}Te_{0.24}Er_{0.015}O_n$$

was prepared in substantially the same manner as in Example 15 except that 19.53 g of erbium nitrate [Er(NO$_3$)$_3$.5H$_2$O] was used instead of the ytterbium nitrate [Yb(NO$_3$)$_3$.4H$_2$O].
(Ammoxidation of Propane)

Using the catalyst obtained above, ammoxidations of propane were serially conducted under substantially the same conditions as in Example 15. The results of the ammoxidations are shown in Table 3.

EXAMPLE 19
(Preparation of an Ammoxidation Catalyst)

An ammoxidation catalyst comprising a silica carrier having supported thereon a compound oxide, wherein the silica carrier is present in an amount of 30% by weight in terms of SiO$_2$, based on the total weight of the compound oxide and the silica carrier, and wherein the compound oxide is represented by the formula:

$$Mo_{1.0}V_{0.34}Nb_{0.14}Te_{0.24}Nd_{0.015}O_n$$

was prepared in substantially the same manner as in Example 15 except that 19.31 g of neodymium nitrate [Nd(NO$_3$)$_3$.6H$_2$O] was used instead of the ytterbium nitrate [Yb(NO$_3$)$_3$.4H$_2$O].
(Ammoxidation of Propane)

Using the catalyst obtained above, ammoxidations of propane were serially conducted under substantially the same conditions as in Example 15. The results of the ammoxidations are shown in Table 3.

EXAMPLE 20
(Preparation of an Ammoxidation Catalyst)

An ammoxidation catalyst comprising a silica carrier having supported thereon a compound oxide, wherein the silica carrier is present in an amount of 30% by weight in terms of SiO$_2$, based on the total weight of the compound oxide and the silica carrier, and wherein the compound oxide is represented by the formula:

$$Mo_{1.0}V_{0.34}Nb_{0.14}Te_{0.24}Sm_{0.015}O_n$$

was prepared in substantially the same manner as in Example 15 except that 19.58 g of samarium nitrate [Sm(NO$_3$)$_3$.6H$_2$O] was used instead of the ytterbium nitrate [Yb(NO$_3$)$_3$.4H$_2$O].

(Ammoxidation of Propane)

Using the catalyst obtained above, ammoxidations of propane were serially conducted under substantially the same conditions as in Example 15. The results of the ammoxidations are shown in Table 3.

TABLE 1

| | Composition of ammoxidation catalyst | R[1] = 1.2 | | R = 1.0 | | R = 0.8 | |
|---|---|---|---|---|---|---|---|
| | | Y(C$_3$)[2] | Y(NH$_3$)[3] | Y(C$_3$) | Y(NH$_3$) | Y(C$_3$) | Y(NH$_3$) |
| Ex. 1 | Mo$_{1.0}$V$_{0.34}$Nb$_{0.14}$Te$_{0.24}$Yb$_{0.010}$O$_n$ | 57.1 | 47.6 | 56.8 | 56.8 | 56.3 | 70.4 |
| Comp. Ex. 1 | Mo$_{1.0}$V$_{0.34}$Nb$_{0.14}$Te$_{0.24}$O$_n$ | 55.3 | 46.1 | 54.3 | 54.3 | 51.6 | 64.5 |

Note: Reaction conditions for ammoxidation using a fixed-bed rector (inner diameter: 10 mm) in Ex. 1 and Comp. Ex. 1:
temperature = 440° C.;
pressure = atmospheric pressure;
contact time = 1.0 sec · g/cc;
[propane:ammonia:oxygen:helium] molar ratio = 1:(1.2, 1.0 and 0.8):2.8:12
Note 1): R means the molar ratio of the fed ammonia to the fed propane.
Note 2): Y(C$_3$) means the propane-based yield (%) of acrylonitrile.
Note 3): Y(NH$_3$) means the ammonia-based yield (%) of acrylonitrile.

TABLE 2

|  | Composition of ammoxidation catalyst | $R^{1)} = 1.0$ | | $R = 0.8$ | |
| --- | --- | --- | --- | --- | --- |
|  |  | $Y(C_3)^{2)}$ | $Y(NH_3)^{3)}$ | $Y(C_3)$ | $Y(NH_3)$ |
| Ex. 2 | $Mo_{1.0}V_{0.34}Nb_{0.14}Te_{0.24}Dy_{0.015}O_n$ | 56.5 | 56.5 | 56.2 | 70.3 |
| Ex. 3 | $Mo_{1.0}V_{0.34}Nb_{0.14}Te_{0.24}Er_{0.015}O_n$ | 56.3 | 56.3 | 55.9 | 69.9 |
| Ex. 4 | $Mo_{1.0}V_{0.34}Nb_{0.14}Te_{0.24}Nd_{0.013}O_n$ | 55.8 | 55.8 | 55.3 | 69.1 |
| Ex. 5 | $Mo_{1.0}V_{0.34}Nb_{0.14}Te_{0.24}Sm_{0.013}O_n$ | 55.6 | 55.6 | 55.0 | 68.8 |
| Ex. 6 | $Mo_{1.0}V_{0.34}Nb_{0.14}Te_{0.24}La_{0.010}O_n$ | 55.4 | 55.4 | 54.9 | 68.6 |
| Ex. 7 | $Mo_{1.0}V_{0.34}Nb_{0.14}Te_{0.24}Pr_{0.011}O_n$ | 55.6 | 55.6 | 55.1 | 68.9 |
| Ex. 8 | $Mo_{1.0}V_{0.34}Nb_{0.14}Te_{0.24}Eu_{0.012}O_n$ | 55.5 | 55.5 | 54.9 | 68.6 |
| Ex. 9 | $Mo_{1.0}V_{0.34}Nb_{0.14}Te_{0.24}Gd_{0.015}O_n$ | 55.1 | 55.1 | 54.6 | 68.3 |
| Ex. 10 | $Mo_{1.0}V_{0.34}Nb_{0.14}Te_{0.24}Tb_{0.012}O_n$ | 55.3 | 55.3 | 54.7 | 68.4 |
| Ex. 11 | $Mo_{1.0}V_{0.34}Nb_{0.14}Te_{0.24}Ho_{0.011}O_n$ | 55.1 | 55.1 | 54.9 | 68.6 |
| Ex. 12 | $Mo_{1.0}V_{0.34}Nb_{0.14}Te_{0.24}Tm_{0.012}O_n$ | 55.8 | 55.8 | 55.1 | 68.9 |
| Ex. 13 | $Mo_{1.0}V_{0.34}Nb_{0.14}Te_{0.24}Lu_{0.013}O_n$ | 55.2 | 55.2 | 54.7 | 68.4 |
| Ex. 14 | $Mo_{1.0}V_{0.34}Nb_{0.14}Te_{0.24}Sc_{0.005}O_n$ | 55.0 | 55.0 | 54.4 | 68.0 |
| Comp. Ex. 2 | $Mo_{1.0}V_{0.34}Nb_{0.14}Te_{0.24}Yb_{0.200}O_n$ | 42.1 | 42.1 | 40.9 | 51.1 |

Note: Reaction conditions for ammoxidation using a fixed-bed rector (inner diameter: 10 mm) in Ex. 2 to 14 and Comp. Ex. 1:
temperature = 440° C.;
pressure = atmospheric pressure;
contact time = 1.0 sec · g/cc;
[propane:ammonia:oxygen:helium] molar ratio = 1:(1.0 and 0.8):2.8:12
Note 1): R means the molar ratio of the fed ammonia to the fed propane.
Note 2): $Y(C_3)$ means the propane-based yield (%) of acrylonitrile.
Note 3): $Y(NH_3)$ means the ammonia-based yield (%) of acrylonitrile.

TABLE 3

|  | Composition of ammoxidation catalyst | $R^{1)} = 1.0$ | | $R = 0.8$ | |
| --- | --- | --- | --- | --- | --- |
|  |  | $Y(C_3)^{2)}$ | $Y(NH_3)^{3)}$ | $Y(C_3)$ | $Y(NH_3)$ |
| Ex. 15 | $Mo_{1.0}V_{0.34}Nb_{0.14}Te_{0.24}Yb_{0.015}O_n/SiO_2$ | 52.1 | 52.1 | 51.7 | 64.6 |
| Comp. Ex. 3 | $Mo_{1.0}V_{0.34}Nb_{0.14}Te_{0.24}O_n/SiO_2$ | 50.8 | 50.8 | 48.7 | 60.9 |
| Ex. 16 | $Mo_{1.0}V_{0.34}Nb_{0.14}Te_{0.24}Yb_{0.020}O_n/SiO_2$ | 52.2 | 52.2 | 51.8 | 64.8 |
| Ex. 17 | $Mo_{1.0}V_{0.34}Nb_{0.14}Te_{0.24}Dy_{0.015}O_n/SiO_2$ | 52.2 | 52.2 | 51.6 | 64.5 |
| Ex. 18 | $Mo_{1.0}V_{0.34}Nb_{0.14}Te_{0.24}Er_{0.015}O_n/SiO_2$ | 52.1 | 52.1 | 51.4 | 64.3 |
| Ex. 19 | $Mo_{1.0}V_{0.34}Nb_{0.14}Te_{0.24}Sm_{0.015}O_n/SiO_2$ | 51.9 | 51.9 | 51.3 | 64.1 |
| Ex. 20 | $Mo_{1.0}V_{0.34}Nb_{0.14}Te_{0.24}Nd_{0.015}O_n/SiO_2$ | 51.9 | 51.9 | 51.2 | 64.0 |

Note: Reaction conditions for ammoxidation using a fluidized-bed rector (inner diameter: 25 mm) in Ex. 15 to 20 and Comp. Ex. 3:
temperature = 440° C.;
pressure = atmospheric pressure;
contact time = 1.0 sec · g/cc;
[propane:ammonia:oxygen:helium] molar ratio = 1:(1.0 and 0.8):2.8:12
Note 1): R means the molar ratio of the fed ammonia to the fed propane.
Note 2): $Y(C_3)$ means the propane-based yield (%) of acrylonitrile.
Note 3): $Y(NH_3)$ means the ammonia-based yield (%) of acrylonitrile.
Note 4): In Examples 15 to 20 and Comparative Example 3, the amount of the silica carrier ($SiO_2$) is 30 wt %.

INDUSTRIAL APPLICABILITY

The ammoxidation catalyst of the present invention can be easily produced and also provides a great advantage wherein the ammonia-based yield of acrylonitrile or methacrylonitrile can be increased without sacrificing the propane- or isobutane-based yield of acrylonitrile or methacrylonitrile, so that both an efficient utilization of the feedstock ammonia and an efficient utilization of the feedstock propane or isobutane can be simultaneously achieved.

What is claimed is:

1. An ammoxidation catalyst for use in producing acrylonitrile or methacrylonitrile from propane or isobutane by ammoxidation in the gaseous phase, comprising a compound oxide represented by the following formula (1):

$$Mo_{1.0}V_aNb_bX_cZ_dE_eO_n \qquad (1)$$

wherein:
X is at least one element selected from the group consisting of tellurium and antimony;
Z is at least one element selected from the group consisting of ytterbium, dysprosium and erbium;
E is at least one element selected from the group consisting of neodymium, samarium, lanthanum, praseodymium, europium, gadolinium, terbium, holmium, thulium, lutetium and scandium; and
a, b, c, d, e and n are, respectively, the atomic ratios of vanadium, niobium, X, Z, E and oxygen, relative to molybdenum,
wherein:
$0.1 \leq a \leq 1.0$;

$0.1 \leq b \leq 1.0$;
$0.1 \leq c \leq 1.0$;
$0.001 \leq d \leq 0.1$;
$0 \leq e \leq 0.1$;
$0.001 \leq d+e \leq 0.1$; and n is a number determined by and consistent with the valence requirements of the other elements present in the compound oxide of formula (1).

2. The catalyst according to claim 1, wherein X in formula (1) is tellurium.

3. The catalyst according to any one of claims 1 or 2, wherein Z in formula (1) is ytterbium.

4. The catalyst according to any one of claims 1 or 2, which further comprises a silica carrier having supported thereon said compound oxide, wherein said silica carrier is present in an amount of from 20 to 60% by weight in terms of $SiO_2$, based on the total weight of said compound oxide and said silica carrier.

5. A process for producing acrylonitrile or methacrylonitrile, which comprises reacting propane or isobutane with ammonia and molecular oxygen in the gaseous phase in the presence of an ammoxidation catalyst comprising a compound oxide represented by the following formula (1):

$$Mo_{1.0}V_aNb_bX_cZ_dE_eO_n \qquad (1)$$

wherein:
X is at least one element selected from the group consisting of tellurium and antimony;
Z is at least one element selected from the group consisting of ytterbium, dysprosium and erbium;
E is at least one element selected from the group consisting of neodymium, samarium, lanthanum, praseodymium, europium, gadolinium, terbium, holmium, thulium, lutetium and scandium; and
a, b, c, d, e and n are, respectively, the atomic ratios of vanadium, niobium, X, Z, E and oxygen, relative to molybdenum,
wherein:
$0.1 \leq a \leq 1.0$;
$0.01 \leq b \leq 1.0$;
$0.01 \leq c \leq 1.0$;
$0.001 \leq d \leq 0.1$;
$0 \leq e \leq 0.1$;
$0.001 \leq d+e \leq 0.1$; and n is a number determined by and consistent with the valence requirements of the other elements present in the compound oxide of formula (1).

6. A process according to claim 6, wherein X in formula (1) is tellurium.

7. A process according to any one of claims 5 or 6, wherein Z in formula (1) is ytterbium.

8. A process according to any one of claims 5 or 6, wherein said catalyst further comprises a silica carrier having supported thereon said compound oxide, wherein said silica carrier is present in an amount of from 20 to 60% by weight in terms of $SiO_2$, based on the total weight of said compound oxide and said silica carrier.

* * * * *

UNITED STATES PATENT AND TRADEMARK OFFICE
CERTIFICATE OF CORRECTION

PATENT NO.     : 6,043,186
DATED          : March 28, 2000
INVENTOR(S)    : Satoru Komada et al.

It is certified that error appears in the above-identified patent and that said Letters Patent is hereby corrected as shown below:

Column 23,
Line 2, "$0.1 \leq c \leq 1.0;$" should read -- $0.01 \leq c \leq 1.0;$ --.

Signed and Sealed this

Sixth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,043,186
DATED : March 28, 2000
INVENTOR(S) : Satoru Komada et al.

It is certified that error appears in the above-identified patent and that said Letters Patent is hereby corrected as shown below:

Column 23,
Line 1, "$0.1 \leq b \leq 1.0$;" should read -- $0.01 \leq b \leq 1.0$; --.

Signed and Sealed this

Twenty-eighth Day of February, 2006

JON W. DUDAS
*Director of the United States Patent and Trademark Office*